United States Patent [19]

Rayhack

[11] Patent Number: 5,176,685

[45] Date of Patent: Jan. 5, 1993

[54] PRECISION BONE CUTTING GUIDE

[76] Inventor: John M. Rayhack, 13919 Shady Shores Dr., Tampa, Fla. 33613

[21] Appl. No.: 638,788

[22] Filed: Feb. 4, 1991

Related U.S. Application Data

[63] Continuation of Ser. No. 428,831, Oct. 30, 1989, Pat. No. 5,042,983.

[51] Int. Cl.⁵ .............................................. A61B 17/00
[52] U.S. Cl. ...................................... 606/87; 606/105; 606/53; 606/82; 606/96
[58] Field of Search ................. 606/79, 80, 82, 87–89, 606/105, 96–98, 176–179, 53

[56] References Cited

U.S. PATENT DOCUMENTS

| | | | |
|---|---|---|---|
| 4,565,192 | 1/1986 | Shapiro | 606/82 |
| 4,703,751 | 11/1987 | Pohl | 606/87 |
| 4,718,413 | 1/1988 | Johnson | 606/82 |
| 4,757,810 | 7/1988 | Reese | 606/87 |
| 4,759,350 | 7/1988 | Dunn et al. | 606/82 |
| 4,892,093 | 1/1990 | Zarnowski et al. | 606/82 |
| 5,049,149 | 9/1991 | Schmidt | 606/87 |

Primary Examiner—Robert A. Hafer
Assistant Examiner—Kerry Owens
Attorney, Agent, or Firm—Dominik, Stein, Saccocio, Reese, Colitz & Van Der Wall

[57] ABSTRACT

The bone saw guide of this invention allows precise perpendicular or angular cutting of a bone with a conventional bone saw. An inverted U-shaped blade guide portion positions the blade and an upstanding saw guide portion guides the neck of the saw. A plate connects the two portions. The invention allows a bone segment to be removed and the cut ends to be compressed together to shorten the bone.

7 Claims, 4 Drawing Sheets

PRECISION BONE CUTTING GUIDE

This is a continuation of copending application Ser. No. 07/428,831 filed on Oct. 30, 1989, now U.S. Pat. No. 5,042,963.

BACKGROUND OF THE INVENTION

1. Field of the Invention

This invention relates to bone saw guides for cutting a bone. More particularly, this invention relates to bone saw guides for angularly cutting a bone, in parallel cuts, allowing a bone segment to be removed and the complementary cut ends compressed together to shorten the bone.

2. Description of the Background Art

During bone shortening, it is often difficult to free-handedly cut a bone with a hand held saw, at precisely parallel cuts, so that a bone segment can be removed and the complementary ends of the bone compressed together at perfectly matching angles. Improper matching upon compression results in gaps in the compressed bone ends and therefore requires excessive healing time.

It ca be readily appreciated that considerable skill is required to properly position the saw blade so that two parallel cuts are made through the bone at the desired angle and location along the longitudinal length of the bone.

Double-bladed bone saws have been developed to facilitate removal of bone segments. Basically, double-bladed bone saws comprise two parallel saw blades spaced apart from each other by a distance equal to the thickness of the bone segment to be removed and fixedly connected to a drive shaft. A motor rotates or oscillates the drive shaft causing simultaneous rotation or oscillation of the parallel blades. When freehandedly positioned against a bone, the blades simultaneously saw two parallel cuts in the bone. When cut through, the resulting bone segment is removed. Unfortunately, double-bladed saws must still be positioned freehandedly and are therefore subject to cutting the bone segment at a undesired angle or at an undesired location along the longitudinal length of the bone.

Therefore, it is an object of this invention to provide an apparatus which overcomes the aforementioned inadequacies of the prior art devices and provides an improvement which is a significant contribution to the advancement of the bone cutting art.

Another object of this invention is to provide a bone saw guide allowing perpendicular or angular cutting of a bone.

Another object of this invention is to provide a bone saw guide allowing the sawing of two parallel cuts through a bone so that a bone segment is removed from the bone.

Another object of this invention is to provide a bone saw guide for cutting a bone segment from a bone at precise angles so that the resulting bone ends are cut at complementary angles for precise matching, with no gaps, when the ends of the bone are compressed together.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of &.he invention may be had by referring to the summary of the invention and the detailed description of the preferred embodiment in addition to the scope of the invention defined by the claims taken in conjunction with the accompanying drawings.

SUMMARY OF THE INVENTION

This invention comprises a bone saw guide allowing the precise perpendicular or angular cutting of a bone with a conventional oscillating bone saw. More particularly, the bone saw guide of the invention comprises a plate for affixing to the bone by means of bone screws which are positioned through holes in the plate and then into previously drilled and tapped holes in the bone. The bone saw guide of the invention further comprises a blade guide portion including a substantially inverted U-shaped configuration having its depending legs spaced apart for straddling the bone therebetween when the plate is affixed to the bone. A plurality of blade slots are formed in the U-shaped blade guide portion to guide the oscillating blade of the conventional oscillating bone saw. The U-shaped blade guide portion is preferably angularly positioned relative to the plate so that cuts at the desired angle are made through the bone.

The bone saw guide of the invention further comprises a saw guide portion including a pair of upstanding guide arms extending upwardly from the plate in a spaced-apart configuration for receiving the cylindrical neck of the bone saw therebetween such that the neck and the bone are coplanar. A surface of each upstanding arms is angled relative to the plate at the same angle as the U-shaped guide portion so that the plane formed by the surface of the arms is parallel to the planes of the blade guides formed in the U-shaped blade portion. In this manner, the blade extending perpendicular from the cylindrical neck of the bone saw remains in alignment with at least one of the blade guides in the U-shaped blade portion during cutting.

An important feature of the bone saw guide of the invention is the precise cutting of the bone which minimizes the need for a steady and precise hand of the surgeon. Moreover, the spacing between the guides can be nonequidistant so different sized bone segments can be removed. For example, the bone saw guide of the invention having three blade guide slots with the second spaced from the first by three centimeters and a third spaced from the second by two centimeters, would allow the removal of a two, three or five centimeter segment of bone. Removal and repositioning of the plate of the bone saw guide to make two parallel cuts is therefore unnecessary.

Another important feature of the bone saw guide of the invention is the compatibility of using the bone saw guide of the invention first to cut and remove a bone segment and then use the bone compression and distraction device of my other invention (described in U.S. patent application, Ser. No. 254,158, filed Oct. 6, 1988 now U.S. Pat. No. 4,929,247, the disclosure of which is hereby incorporated by reference herein) to compress the ends of the bone together. Specifically, this compatibility can be achieved by positioning the fixation screws of the bone compression and distraction device in the same holes as the holes in the plate of the bone saw guide. This allows most of the holes drilled and tapped in the bone for the bone saw guide to be used by the screws needed for the plate of the bone distraction and compression device. Redrilling and tapping of additional holes in the bone is therefore minimized.

Another important feature is the possibility of now placing an interfragmentary screw across the oblique cut thus enhancing stability.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
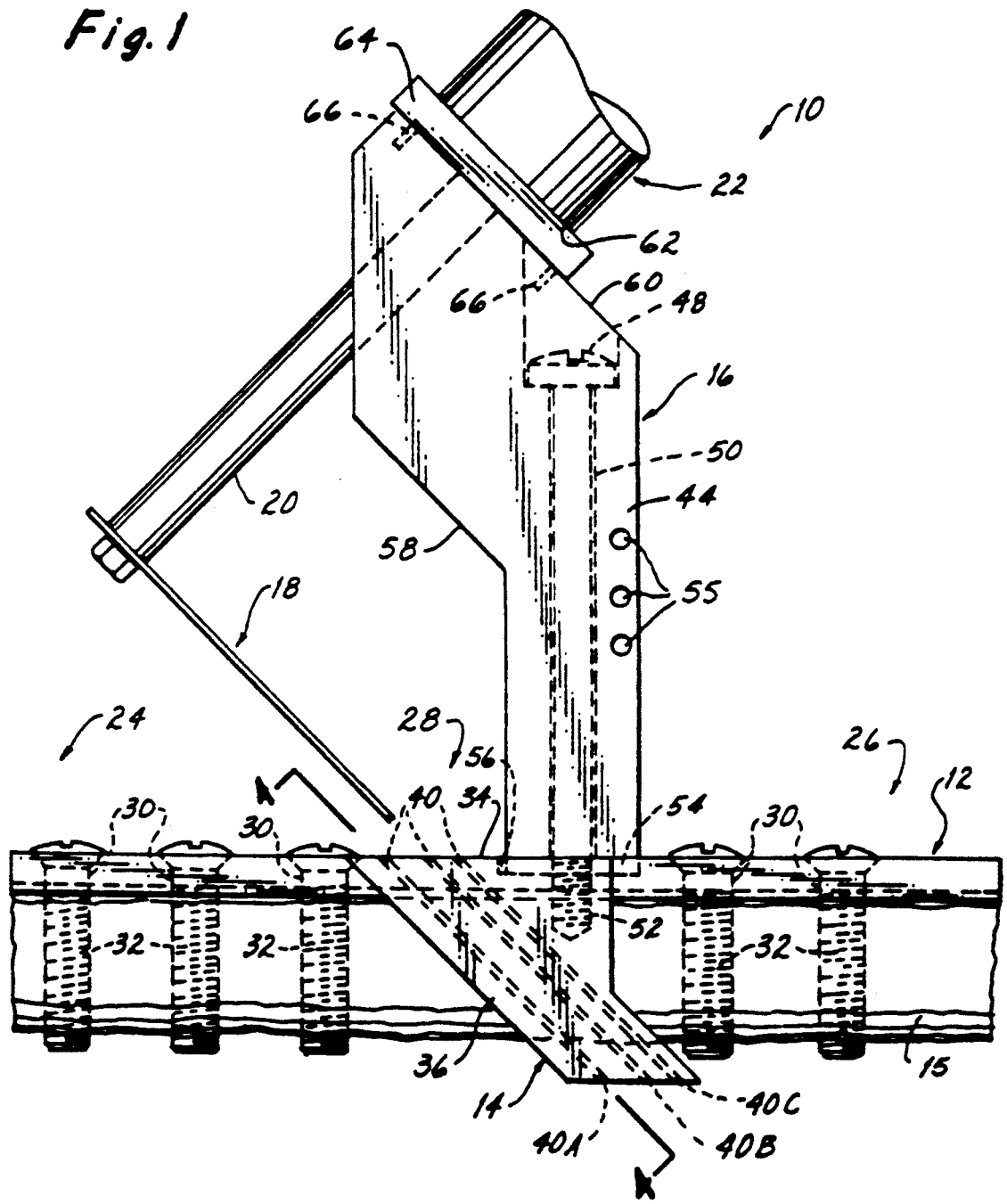
FIG. 1 is a side plan view of the bone saw guide of the invention affixed to the bone to be angularly cut and illustrating a conventional oscillating bone saw.

The bone saw guide 10 of the invention is illustrated in FIGS. 1-5 and comprises a plate 12, an inverted U-shaped blade guide portion 14 depending from the plate 12, and an upstanding saw guide portion 16 extending upwardly from the plate 12. The bone saw guide 10 functions to guide the saw blade 18 perpendicularly connected to the end of an oscillating drive shaft journalled with a cylindrical neck 20 of a conventional oscillating bone saw, generally indicated by numeral 22, into the bone 15 to be cut.

More particularly, as shown in FIG. 1, the plate 12 of the bone saw guide 10 comprises an elongated configuration having a forward portion 24, a rearward portion 26 and a middle portion 28. A plurality of holes 30 are formed in both the forward and rearward portion 24 and 26. Thus, the plate 12 can be rigidly affixed to the bone 15 by means of conventional bone screws 32 which are positioned through holes 30 into previously drilled and tapped holes in the bone 15.

The U-shaped blade guide portion 14 is preferably integrally formed with the middle portion 28 of the plate 12. The U-shaped blade guide portion 14 comprises a horizontal portion 34 positioned transversely to the plate 12 (see FIG. 3) and a pair of legs 36 and 38 depending from the opposing ends of the horizontal portion 34 in a spaced-apart configuration so as to straddle the bone 15 positioned therebetween (see FIG. 2).

Figure 2:
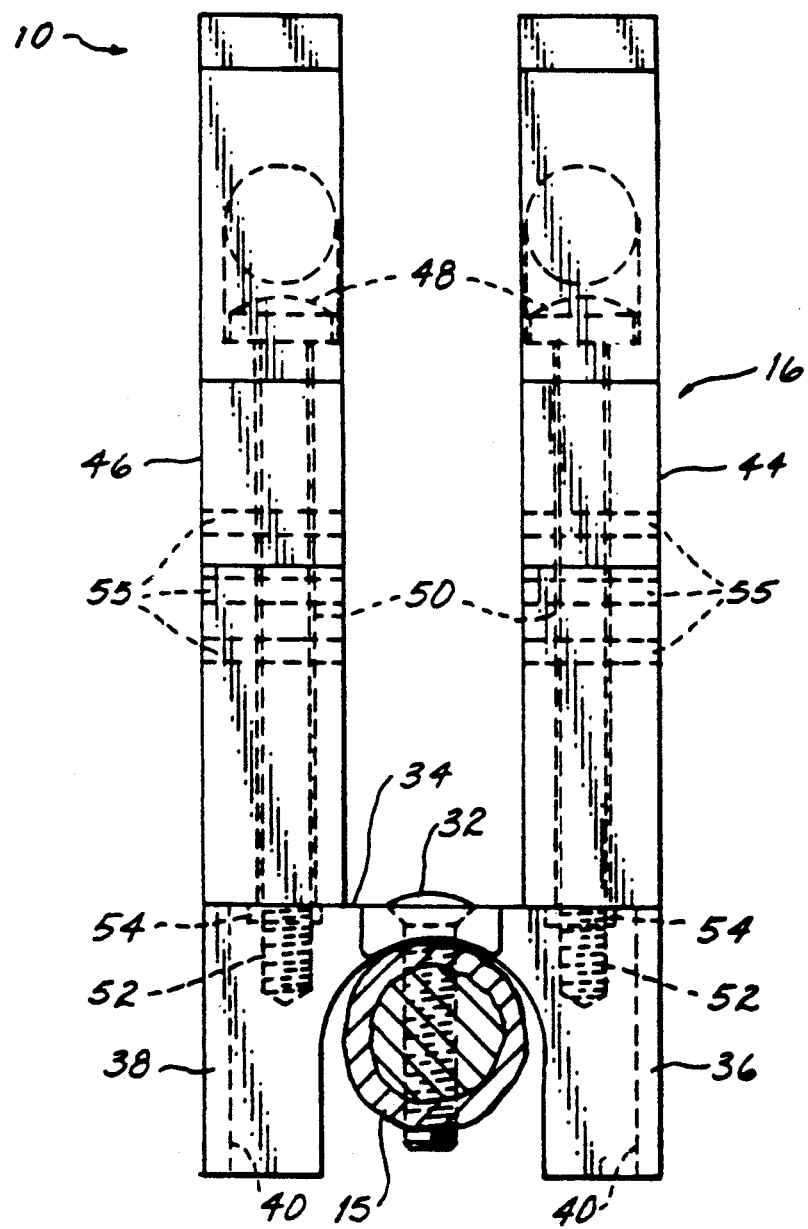
FIG. 2 is a front view of FIG. 1 (bone saw omitted) illustrating the spaced-apart configuration of the depending legs of the blade guide portion which straddle the bone to be cut and the upstanding arms of the saw guide portion for guiding the neck of the bone saw.
Figure 3:
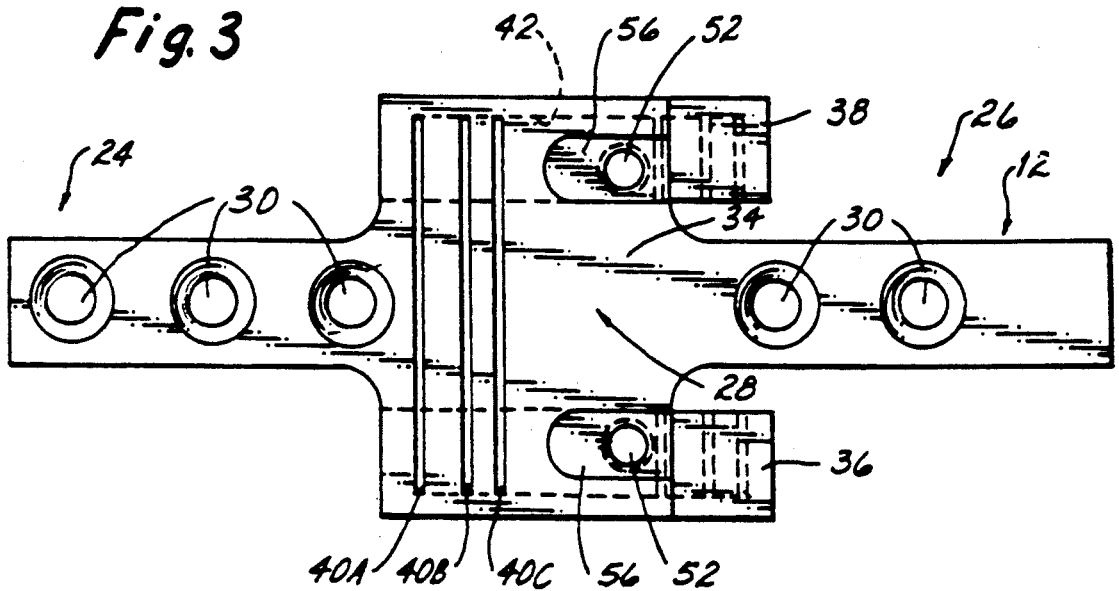
FIG. 3 is a top view of the bone saw guide of the invention with the upstanding arms removed illustrating the positioning of the blade slots in the blade guide portion and the holes in the plate to be affixed to the bone to be cut.
Figure 4:
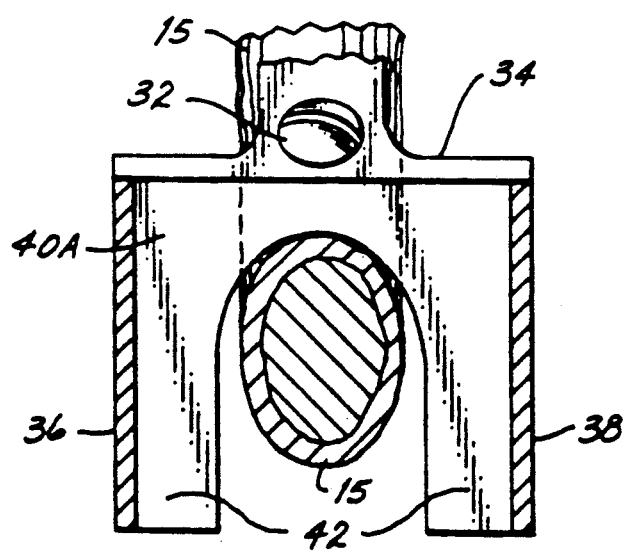
FIG. 4 is a cross sectional view of FIG. 1 along lines 4—4 illustrating the blade slots formed in the U-shaped blade guide portion for guiding the saw blade of the oscillating saw.

As shown in FIGS. 2 and 3, three slots 40A, B and C are positioned through the horizontal portion 34 and into the inner sides 42 of the legs 36 and 38. Each blade slot 40 includes a thickness dimension slightly greater than the thickness of the blade 18 of the bone saw 22 so as to allow the blade 18 to slide therein. Each blade slot 40 includes a width dimension appreciably greater than the amplitude of the oscillation of the blade 18 so as to allow the blade 18 to freely sideways oscillate within the slot 40. Preferably, blade slots 40 are positioned apart from adjacent slots by different dimensions so as to allow different sized bone segments to be cut and removed (see also FIG. 1).

As shown in FIG. 2, the saw guide portion 16 comprises a pair of upstanding arms 44 and 46 positioned spaced-apart from each other for receiving the neck 20 of the saw 22. When configured for angular cutting (e.g. 45 degree oblique angle), the upstanding arms 44 and 46 are rigidly connected to the uppermost surface of the horizontal portion 34 by means of longitudinal screws 48 which are fitted through a longitudinal hole 50 in the longitudinal length of the arms 44 and 46 for threaded engagement into a threaded hole 52 in the horizontal portion 34. The bottom surface of each arm 44 and 46 may include a rectangular protrusion 54 for fitting into a slot 56 in the upper surface of the horizontal portion 34 (see also FIG. 3) to preclude any rotation of the arms 44 and 46 about their respective longitudinal machine screws 48.

As best shown in FIG. 2, the upstanding arms 44 and 46 are preferably configured with the protrusion 54 positioned off set instead of being centered in the bottom surface of the arms 44 and 46. In this manner, the spaced distance between the arms 44 and 46 shown in FIG. 2 can be easily changed to a reduced spacing by interchanging the arms 44 and 46 connected to the horizontal portion 34. This allows bone saws 22 having the two standard sized diameter necks 20 to be used with the bone guide 10 of the invention.

Each arm 44 and 46 comprises an undercut lower portion 58 which provides clearance for the blade 18 being positioned within the selected blade slots 40. Each arm 44 and 46 further includes a sloped surface 60. The plane of the surface 60 is preferably parallel to the planes of the blade slots 40. Noting that the saw blade 18 is parallel to the transverse face 62 of the bone saw 22, the transverse face 62 of the bone saw 22 may rest against the upper surface 0 of the arms 44 and 46 so as to align the blade 18 with the forwardmost blade slot 40A. Three holes 55 in each arm 44 and 46 are provided to receive a pin to control the depth of the cut for each particular slot 40.

A plurality of shims 64 of differing thicknesses are provided for affixing to the surface 60 by means of locator pins 66. The thickness of the shims 64 correspond to the distance of the second and third blade slots 40 from the forwardmost blade slot 40A. Thus, with no shims 64 installed, the transverse face 62 of the bone saw 22 may rest against the upper surfaces 60 of the arms 44 and 46 at which time the blade 18 is in proper alignment with the forwardmost blade slot 40A. As illustrated in FIG. 1, with one shim 64 installed of proper thickness, the blade 18 is aligned with the middle blade slot 40B. Installation of a thicker shim 64 allows alignment of the blade 18 with the rearwardmost blade slot 40C.

Most importantly, an interfragmentary lag bone screw may be threaded into another hole drilled and tapped across the angled cut. Since the angled cut includes a greater cross sectional area, improved healing is expected.

Figure 5:
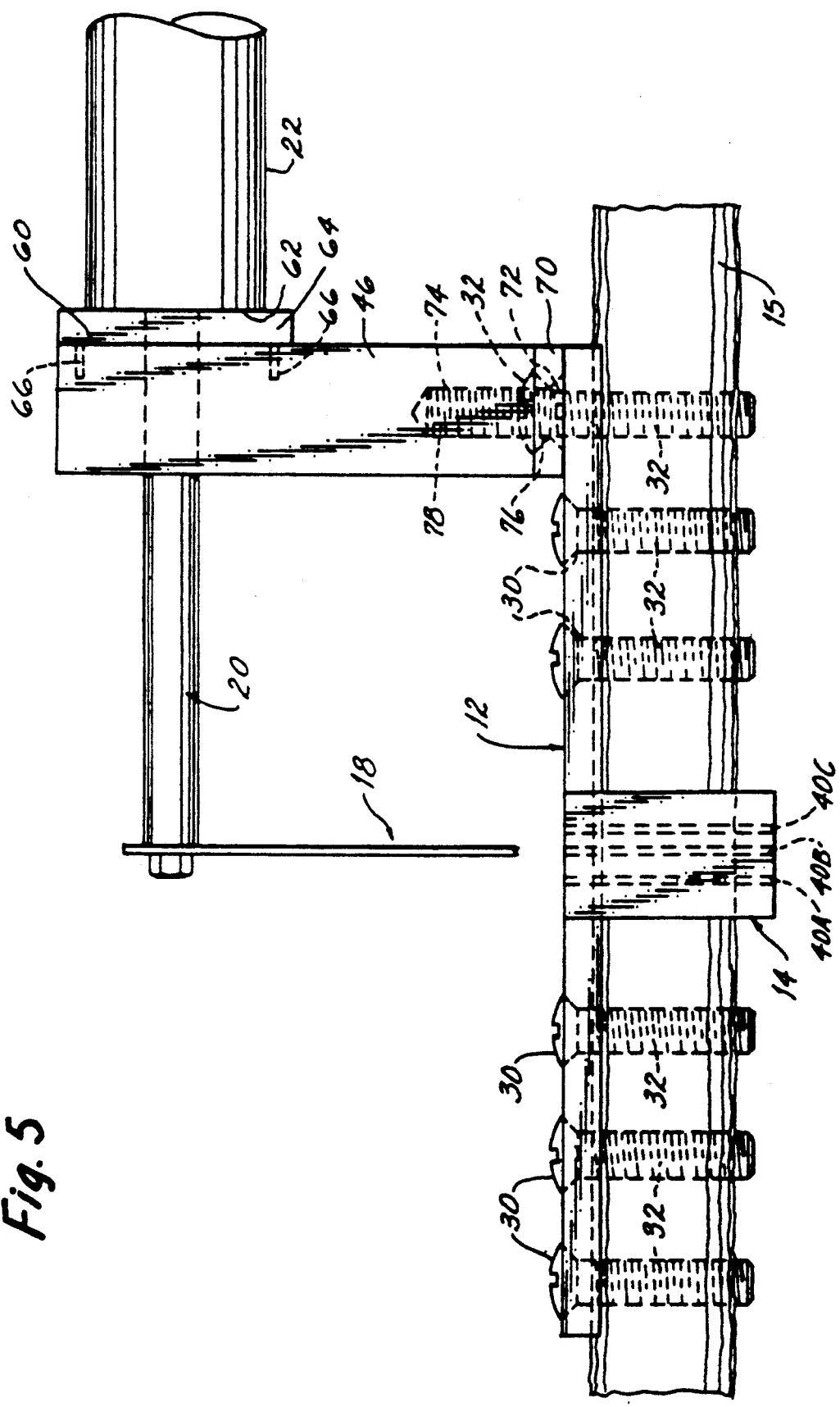
FIG. 5 is a side plan view of the bone saw of the invention affixed to the bone to be perpendicularly cut.

As shown in FIG. 5, when configured for perpendicular cutting, the upstanding arms 44 and 46 are rigidly connected to a horizontal plate 70 positioned transversely to plate 12. Horizontal plate 70 comprises a screw hole 72 allowing the horizontal plate 70 to be affixed to the plate 12 by means of a machine screw 32. The upstanding arms 44 and 46 are rigidly connected to the horizontal plate 70 by means of longitudinal screws 74 which are fitted through holes 76 in the horizontal plate 70 for threaded engagement with threaded holes 78 in the bottom surface of each arm 44 and 46, such that the arms 44 and 46 are positioned spaced apart from each other for receiving the neck 20 of the saw 22.

The surface 60 of each of the arms 44 and 46 is positioned perpendicular to the plate 12. Likewise, the U-shaped blade guide portion 14 described above is positioned such that the blade guide slots 40 are also positioned perpendicular to the plate 12. The upstanding arms 44 and 46 are positioned relative to the blade guide portion 14 such that the transverse face 62 of the bone saw 22 rests against the surface 60 causing the blade 18 to be positioned in alignment with the forwardmost blade slot 40A. As described above, shims 64 of differing thicknesses may be provided for affixing to the surface 60 by means of locator pins 66 such that the transverse face 62 of the saw 22 rests against the shim 64 of the arms 44 and 46 and align the blade 18 with the desired blade slot 40

It is noted that the neck 20 of a conventional bone saw 22 is cylindrical in configuration with the drive shaft (not shown) rotatably journalled therein to which the blade 18 is connected. However, as shown in FIG. 1, it is contemplated that a specially formed neck 20 can be manufactured which is rectangular in cross section with the center of oscillation of the blade 18 being aligned with one of the flat sides of the rectangular neck 20. The center of oscillation is therefore also aligned with the center line of the plate 12 and the blade slots 40.

Finally, it is noted that the spacing of the holes 30 in the plate 12 may be the same as the spacing of the holes 16 and 20 in the slotted plate 12 of my bone distraction and compression device 10 described in my pending patent application referenced hereinabove. This allows the slotted plate 12 to utilize some of the same holes drilled and tapped in the bone 15. Redrilling and tapping holes is therefore minimized.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit of the invention.

Now that the invention has been described,
What is claimed is:

1. A bone saw guide for guiding a blade operatively connected to a neck of a bone saw to cut a bone in two, comprising in combination:
   an elongated plate having a forward portion, a rearward portion and a middle portion therebetween;
   a blade guide portion having a horizontal portion and leg means extending therefrom, said horizontal portion and said leg means including at least one blade slot for receiving and guiding the blade;
   a cutting plane coextensive with said slot and located between said forward portion and rearward portion and through the bone to be cut;
   means for positioning said horizontal portion transverse to said elongated plate at said middle portion; and
   means for independently affixing said forward and rearward portions of said elongated plate to the bone on opposite sides of said cutting plane with said blade slot in alignment over the position at which the bone is to be cut,
   thereby upon positioning the blade into said blade slot and operating the bone saw, the bone is cut precisely in alignment with said blade slot and, after cutting, the ends of the elongated bone thus formed are prevented from movement by said affixing means.

2. The bone saw guide as set forth in claim 1, wherein said affixing means comprises holes positioned in said elongated plate allowing bone threaded fasteners to be positioned therethrough into the bone.

3. The bone saw guide as set forth in claim 1, wherein said blade guide portion includes a plurality of said blade slots positioned parallel to each other.

4. The bone saw guide as set forth in claim 1, wherein said blade slot is perpendicularly positioned relative to said elongated plate.

5. The bone saw guide as set forth in claim 1, wherein said blade slot is angularly positioned relative to said elongated plate.

6. A bone saw guide for guiding a blade operatively connected to a bone saw to cut an elongated bone, comprising in combination:
   an elongated plate having a first hole at one end, a second hole at another end, and a blade guide positioned therebetween, said blade guide including at least one blade slot for receiving and guiding the blade; and
   first and second bone screws for engaging through said first and second holes, respectively, into the elongated bone to rigidly secure said elongated plate to the elongated bone with said blade slot in alignment over the position at which the elongated bone is to be cut,
   whereby, upon positioning the blade into said blade slot and operating the bone saw, the elongated bone is cut precisely in alignment with said blade slot and, after cutting, the ends of the elongated bone thus formed are prevented from movement by said bone screws rigidly engaging into the bone.

7. A method for precisely sawing an elongated bone with a saw blade of a bone saw, comprising the steps of:
   providing an elongated plate having a first hole at one end, a second hole at another end and a blade guide positioned therebetween, the blade guide including at least one blade slot for receiving and guiding the blade;

positioning the elongated plate on the elongated bone with the blade slot in alignment over the position at which the bone is to be cut;

threadably engaging a first bone screw through the first hole into the bone to rigidly secure the one end of the elongated plate to the bone;

threadably engaging a second bone screw through the second hole into the elongated bone to rigidly secure the other end of the elongated plate to the bone; and positioning the blade of the bone saw into the blade slot such that, upon operation of the bone saw, the blade saws the bone in precise alignment with the blade slot while the ends of the elongated bone thus formed are retained in an aligned position by means of the bone screws rigidly securing the elongated plate to the bone.

* * * * *